(12) United States Patent
Flohr et al.

(10) Patent No.: US 7,569,618 B2
(45) Date of Patent: *Aug. 4, 2009

(54) ABSORBENT ARTICLES COMPRISING SURFACE CROSS-LINKED SUPERABSORBENT POLYMER PARTICLES MADE BY A METHOD USING ULTRAVIOLET RADIATION

(75) Inventors: Andreas Flohr, Kronberg (DE); Torsten Lindner, Kronberg (DE); Esther Oliveros, Barbelroth (DE); Yoshiro Mitsukami, Aboshi-ku (JP)

(73) Assignee: The Procter & Gamble Company, Cincinnati, OH (US)

( * ) Notice: Subject to any disclaimer, the term of this patent is extended or adjusted under 35 U.S.C. 154(b) by 0 days.

This patent is subject to a terminal disclaimer.

(21) Appl. No.: 11/508,371

(22) Filed: Aug. 23, 2006

(65) Prior Publication Data

US 2007/0048517 A1 Mar. 1, 2007

(30) Foreign Application Priority Data

Aug. 23, 2005 (EP) ................... 05018251
Jun. 22, 2006 (EP) ................... 06012830

(51) Int. Cl.
C08F 2/46 (2006.01)
C08F 2/50 (2006.01)

(52) U.S. Cl. ............... 522/3; 522/86; 522/87; 522/88; 522/89; 522/90; 522/96; 522/10; 522/103; 522/104; 522/107; 522/113; 522/114; 522/116; 522/120; 522/121; 522/123; 522/134; 522/135; 522/137; 522/141; 522/154; 522/173; 522/175; 522/178; 522/181; 427/508; 427/512; 428/402; 428/403

(58) Field of Classification Search ............... 522/3; 427/508, 512
See application file for complete search history.

(56) References Cited

U.S. PATENT DOCUMENTS

| 3,661,875 | A | 5/1972 | Sieja et al. |
| 4,062,817 | A | 12/1977 | Westerman |
| 4,076,663 | A | 2/1978 | Masuda et al. |
| 4,093,776 | A | 6/1978 | Aoki et al. |
| 4,666,983 | A | 5/1987 | Tsubakimoto et al. |
| 4,734,478 | A | 3/1988 | Tsubakimoto et al. |
| 5,137,537 | A | 8/1992 | Herron et al. |
| 5,147,345 | A | 9/1992 | Young et al. |
| 5,260,345 | A | 11/1993 | Desmarais et al. |
| 5,342,338 | A | 8/1994 | Roe |
| 5,387,207 | A | 2/1995 | Dyer et al. |
| 5,397,316 | A | 3/1995 | Lavon et al. |
| 5,562,646 | A | 10/1996 | Goldman et al. |
| 5,597,873 | A | 1/1997 | Chambers et al. |
| 5,610,208 | A | 3/1997 | Dairoku et al. |
| 5,650,222 | A | 7/1997 | Desmarais et al. |
| 6,359,049 | B1 * | 3/2002 | Carrico et al. ............ 524/414 |
| 7,166,356 | B2 * | 1/2007 | Flohr .................... 428/403 |
| 2006/0252913 | A1 * | 11/2006 | Herfert et al. ............ 528/480 |
| 2007/0048516 | A1 | 3/2007 | Flohr et al. |
| 2007/0048518 | A1 | 3/2007 | Flohr et al. |
| 2007/0049689 | A1 | 3/2007 | Meyer et al. |
| 2007/0203304 | A1 * | 8/2007 | Mitchell ................ 525/330.3 |

FOREIGN PATENT DOCUMENTS

| EP | 1506788 A1 * | 2/2005 |
| EP | 1624002 A | 2/2006 |
| EP | 1757646 A | 2/2007 |
| JP | 56/134960 A | 10/1981 |
| JP | 2003 156961 A | 5/2003 |
| WO | WO-2005/014066 A1 | 2/2005 |
| WO | WO-2005/082429 A2 | 9/2005 |
| WO | WO-2005/082429 A3 | 9/2005 |

OTHER PUBLICATIONS

International Search Report dated Jul. 30, 2008 (4 pages).
International Search Report.

* cited by examiner

Primary Examiner—Sanza L McClendon
(74) Attorney, Agent, or Firm—John P. Colbert

(57) ABSTRACT

A method of surface cross-linking superabsorbent polymer particles using UV irradiation is provided. The method is carried out in a so-called drum reactor, which comprises a hollow drum and an irradiation source. The drum has a longitudinal axis and a cross-section. Radical former molecules are applied on the surface of superabsorbent polymer particles. These superabsorbent polymer particles are fed into the drum and are irradiated while they move within the drum, which is rotated around its longitudinal axis. The irradiation source is provided such that the radiation emitted by the irradiation source is able to reach superabsorbent polymer particles within said drum. The irradiation source for use in the method is able to emit UV radiation of a wavelength between about 201 nm and about 400 nm.

13 Claims, 1 Drawing Sheet

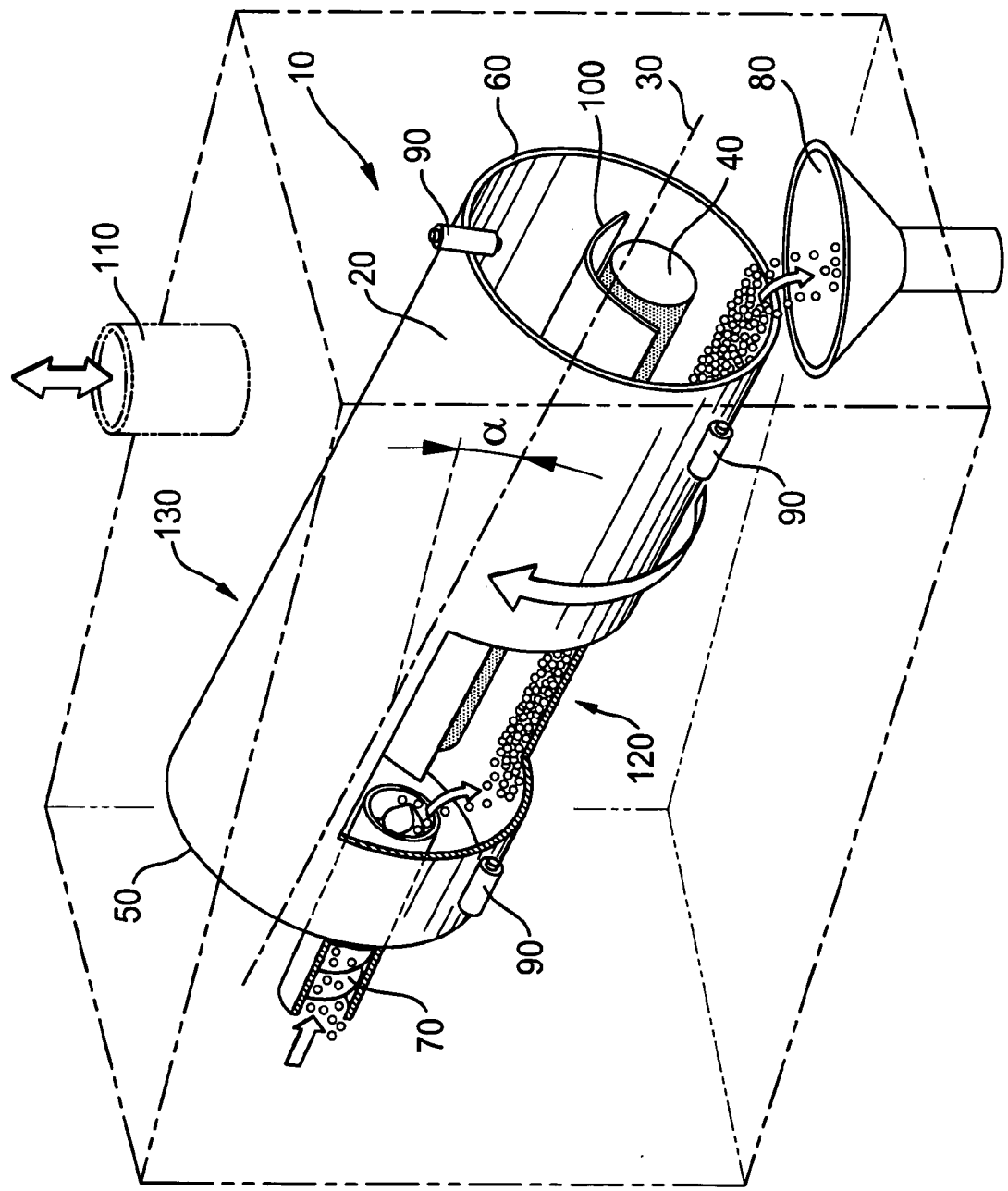

ABSORBENT ARTICLES COMPRISING SURFACE CROSS-LINKED SUPERABSORBENT POLYMER PARTICLES MADE BY A METHOD USING ULTRAVIOLET RADIATION

FIELD OF THE INVENTION

The present application relates to a method for making surface-cross-linked superabsorbent polymer (SAP) particles, using ultraviolet (UV) radiation and being carried out in a drum reactor. The present application also relates to absorbent articles comprising SAP particles made by said method.

BACKGROUND OF THE INVENTION

Superabsorbent polymers (SAPs) are well known in the art. They are commonly applied in absorbent articles, such as diapers, training pants, adult incontinence products and feminine care products to increase the absorbent capacity of such products while reducing their overall bulk. SAPs are capable of absorbing and retaining amounts of aqueous fluids equivalent to many times their own weight.

Commercial production of SAPs began in Japan in 1978. The early superabsorbent was a cross-linked starch-g-polyacrylate. Partially neutralized polyacrylic acid eventually replaced earlier superabsorbents in the commercial production of SAPs, and has become the primary polymer in SAPs. SAPs are often applied in form of small particles. They generally consist of a partially neutralized lightly cross-linked polymer network, which is hydrophilic and permits swelling of the network once submerged in water or an aqueous solution such as physiological saline. The cross-links between the polymer chains assure that the SAP does not dissolve in water.

After absorption of an aqueous solution, swollen SAP particles become very soft and deform easily. Upon deformation the void spaces between the SAP particles are blocked, which drastically increases the flow resistance for liquids. This is generally referred to as "gel-blocking". In gel blocking situations liquid can move through the swollen SAP particles only by diffusion, which is much slower than flow in the interstices between the SAP particles.

One commonly applied way to reduce gel blocking is to make the particles stiffer, which enables the swollen SAP particles to retain their original shape thus creating or maintaining void spaces between the particles. A well-known method to increase stiffness is to cross-link the carboxyl groups exposed on the surface of the SAP particles. This method is commonly referred to as surface cross-linking.

The art refers, for example, to surface cross-linked and surfactant coated absorbent resin particles and a method of their preparation. The surface cross-linking agent can be a polyhydroxy compound comprising at least two hydroxyl groups, which react with the carboxyl groups on the surface of the SAP particles. In some art, surface cross-linking is carried out at temperatures of 150° C. or above.

A water-soluble peroxide radical initiator as surface cross-linking agent is also known. An aqueous solution containing the surface cross-linking agent is applied on the surface of the polymer. The surface cross-linking reaction is achieved by heating to a temperature such that the peroxide radical initiator is decomposed while the polymer is not decomposed.

More recently the use of an oxetane compound and/or an imidazolidinone compound for use as surface cross-linking agent has been disclosed. The surface cross-linking reaction can be carried out under heat, wherein the temperature is preferably in the range of 60° C. to 250° C. Alternatively, the surface cross-linking reaction can also be achieved by a photo-irradiation treatment, preferably using ultraviolet rays.

In general, the surface cross-linking agent is applied onto the surface of the SAP particles. Therefore, the reaction preferably takes place on the surface of the SAP particles, which results in improved cross-linking on the surface of the particles while not substantially affecting the core of the particles. Hence, the SAP particles become stiffer and gel-blocking is reduced.

A drawback of the commercial surface cross-linking process described above is, that it takes relatively long, commonly at least about 30 min. However, the more time is required for the surface cross-linking process, the more surface cross-linking agent will penetrate into the SAP particles, resulting in increased cross-linking inside the particles, which has a negative impact on the capacity of the SAP particles. Therefore, it is desirable to have short process times for surface cross-linking. Furthermore, short process times are also desirable with respect to an overall economic SAP particle manufacturing process.

Another drawback of common surface cross-linking processes is, that they take place only under relatively high temperatures, often around 150° C. or above. At these temperatures, not only the surface cross-linker reacts with the carboxyl groups of the polymer, but also other reactions are activated, such as anhydride-formation of neighbored carboxyl groups within or between the polymer chains, and dimer cleavage of acrylic acid dimers incorporated in the SAP particles. Those side reactions also affect the core, decreasing the capacity of the SAP particles. In addition, exposure to elevated temperatures can lead to color degradation of the SAP particles. Therefore, these side reactions are generally undesirable.

SAPs known in the art are typically partially neutralized, for example, with sodium hydroxide. However, neutralization has to be carefully balanced with the need for surface cross-linking: The surface cross-linking agents known in the art react with free carboxyl groups comprised by the polymer chains at relatively. high speed but react with a neutralized carboxyl groups only very slowly. Thus, given carboxyl groups can either be applied for surface cross-linking or for neutralization, but not for both. Surface cross-linking agents known in the art preferably react with the chemical group carboxyl groups, they do not react with aliphatic groups.

In the process of making SAP particles, neutralization of free carboxyl groups typically comes first, before surface cross-linking takes place. Indeed, the neutralization step is often carried out in the very beginning of the process, before the monomers are polymerized and cross-linked to form the SAP. Such a process is named "pre-neutralization process". Alternatively, the SAP can be neutralized during polymerization or after polymerization ("post-neutralization"). Furthermore, a combination of these alternatives is also possible.

The overall number of free carboxyl groups on the outer surface of the SAP particles is limited by the foregoing neutralization but it is believed that the free carboxyl groups are also not homogeneously distributed. Hence, it is currently difficult to obtain SAP particles with evenly distributed surface cross-linking. On the contrary, often SAP particles have regions of rather dense surface cross-linking, for example, with a relatively high number of surface cross-links, and regions of sparsely surface cross-linking. This inhomogeneity has a negative impact on the desired overall stiffness of the SAP particles.

In one embodiment, a method of making SAP particles with evenly distributed, homogenous surface cross-linking is provided.

Moreover, it is difficult to obtain SAP particles having both, sufficient stiffness to avoid gel blocking (sometimes referred to as "gel strength") and sufficient swelling capacity (sometimes referred to as "gel volume"). Typically, increasing the gel strength of the SAP particles has a negative impact on the gel volume and vice versa.

In another embodiment, the surface cross-links are restricted to the very surface of the SAP particles in order to minimize the decrease in capacity. Thus, the core of the SAP particles should not be considerably affected and the additional cross-links introduced in the core should be kept to a minimum.

In another embodiment, a method of surface cross-linking SAP particles is provided, which can be carried out quickly to increase the efficiency of the method.

In another embodiment, a method of surface cross-linking SAP particles is provided, which can be carried out at moderate temperatures in order to reduce undesired side reactions, such as anhydride-formation and dimer cleavage.

SUMMARY OF THE INVENTION

In one embodiment, a method of surface cross-linking superabsorbent polymer particles is provided, the method comprising the steps of:
a) providing superabsorbent polymer particles and providing radical former molecules applied onto the superabsorbent polymer particles;
b) providing a reactor comprising a drum;
c) feeding the superabsorbent polymer particles with the radical former molecules added thereon into the drum;
d) moving the superabsorbent polymer particles with the radical former molecules added thereon in the drum by rotating the drum around its longitudinal axis;
e) the superabsorbent polymer particles with the radical former molecules added thereon being irradiated by the irradiation source as the particles are moved within the drum; and
f) collecting the superabsorbent polymer particles leaving the drum. The drum has a longitudinal axis and further has a cross-section. An irradiation source is provided such that the radiation emitted by the irradiation source is able to reach superabsorbent polymer particles within the drum and the irradiation source is able to emit UV radiation of a wavelength between about 201 nm and about 400 nm.

BRIEF DESCRIPTION OF THE DRAWINGS

While the specification concludes with claims pointing out and distinctly claiming the invention, it is believed the same will be better understood by the following drawings taken in conjunction with the accompanying specification wherein like components are given the same reference number.

FIG. 1 is schematic drawing of an exemplary drum reactor in accordance with one embodiment.

DETAILED DESCRIPTION OF THE INVENTION

In one embodiment, the SAPs comprise a homo-polymer of partially neutralized α,β-unsaturated carboxylic acid or a copolymer of partially neutralized α,β-unsaturated carboxylic acid copolymerized with a monomer co-polymerizable therewith. Furthermore, the homo-polymer or copolymer comprised by the SAP comprises aliphatic groups, wherein at least some of the aliphatic groups are at least partially comprised by the surface of the SAP particles.

SAPs are available in a variety of chemical forms, including substituted and unsubstituted natural and synthetic polymers, such as carboxymethyl starch, carboxymethyl cellulose, and hydroxypropyl cellulose; nonionic types such as polyvinyl alcohol, and polyvinyl ethers; cationic types such as polyvinyl pyridine, polyvinyl morpholinione, and N,N-dimethylaminoethyl or N,N-diethylaminopropyl acrylates and methacrylates, and the respective quaternary salts thereof. Typically, SAPs useful herein have a multiplicity of anionic, functional groups, such as sulfonic acid, and more typically carboxyl groups. Examples of polymers suitable for use herein include those, which are prepared from polymerizable, unsaturated, acid-containing monomers. Thus, such monomers include the olefinically unsaturated acids and anhydrides that contain at least one carbon-to-carbon olefinic double bond. More specifically, these monomers can be selected from olefinically unsaturated carboxylic acids and acid anhydrides, olefinically unsaturated sulfonic acids, and mixtures thereof.

Some non-acid monomers can also be included, usually in minor amounts, in preparing SAPs. Such non-acid monomers can include, for example, the water-soluble or water-dispersible esters of the acid-containing monomers, as well as monomers that contain no carboxylic or sulfonic acid groups at all. Optional non-acid monomers can thus include monomers containing the following types of functional groups: carboxylic acid or sulfonic acid esters, hydroxyl groups, amide-groups, amino groups, nitrile groups, quaternary ammonium salt groups, aryl groups (e.g., phenyl groups, such as those derived from styrene monomer). These non-acid monomers are well-known materials and are described in greater detail, for example, in U.S. Pat. Nos. 4,076,663 and in 4,062,817.

Olefinically unsaturated carboxylic acid and carboxylic acid anhydride monomers include the acrylic acids typified by acrylic acid itself, methacrylic acid, ethacrylic acid, α-chloroacrylic acid, α-cyanoacrylic acid, β-methylacrylic acid (crotonic acid), α-phenylacrylic acid, β-acryloxypropionic acid, sorbic acid, α-chlorosorbic acid, angelic acid, cinnamic acid, p-chlorocinnamic acid, β-sterylacrylic acid, itaconic acid, citroconic acid, mesaconic acid, glutaconic acid, aconitic acid, maleic acid, fumaric acid, tricarboxyethylene and maleic acid anhydride.

Olefinically unsaturated sulfonic acid monomers include aliphatic or aromatic vinyl sulfonic acids such as vinylsulfonic acid, allyl sulfonic acid, vinyl toluene sulfonic acid and styrene sulfonic acid; acrylic and methacrylic sulfonic acid such as sulfoethyl acrylate, sulfoethyl methacrylate, sulfopropyl acrylate, sulfopropyl methacrylate, 2-hydroxy-3-methacryloxypropyl sulfonic acid and 2-acrylamide-2-methylpropane sulfonic acid.

In one embodiment, SAPs contain carboxyl groups. These polymers comprise hydrolyzed starch-acrylonitrile graft copolymers, partially neutralized hydrolyzed starch-acrylonitrile graft copolymers, starch-acrylic acid graft copolymers, partially neutralized starch-acrylic acid graft copolymers, saponified vinyl acetate-acrylic ester copolymers, hydrolyzed acrylonitrile or acrylamide copolymers, slightly network crosslinked polymers of any of the foregoing copolymers, partially neutralized polyacrylic acid, and slightly network cross-linked polymers of partially neutralized polyacrylic acid, partially neutralized polymethacrylic acid, and slightly network cross-linked polymers of partially neutralized polymethacrylic acid. These polymers can be used either solely or in the form of a mixture of two or more different polymers, that when used as mixtures, individually do not have to be partially neutralized, whereas the resulting copolymer has to be. Examples of these polymer materials are disclosed in U.S. Pat. Nos. 3,661,875, 4,076,663, 4,093,776, 4,666,983, and 4,734,478.

In one example, polymer materials for use herein are slightly network cross-linked polymers of partially neutralized polyacrylic acids, slightly network cross-linked polymers of partially neutralized polymethacrylic acids, their copolymers and starch derivatives thereof. SAPs comprise partially neutralized, slightly network cross-linked, polyacrylic acid (for example, poly(sodium acrylate/acrylic acid)). In one embodiment the SAPs are at least about 50 mol-%, in another embodiment at least about 70 mol-%, in another embodiment at least about 75 mol-% and in yet another embodiment from about 75 mol-% to about 95 mol-% neutralized. Network cross-linking renders the polymer substantially water-insoluble and, in part, determines the absorptive capacity of the hydrogel-forming absorbent polymers. Processes for network cross-linking these polymers and typical network cross-linking agents are described in greater detail in U.S. Pat. No. 4,076,663.

A suitable method for polymerizing the $\alpha,\beta$-unsaturated carboxylic acid monomers is aqueous solution polymerization, which is well known in the art. An aqueous solution comprising $\alpha,\beta$-unsaturated carboxylic acid monomers and polymerization initiator is subjected to a polymerization reaction. The aqueous solution may also comprise further monomers, which are co-polymerizable with the $\alpha,\beta$-unsaturated carboxylic acid monomers. At least the $\alpha,\beta$-unsaturated carboxylic acid has to be partially neutralized, either prior to polymerization of the monomers, during polymerization or post polymerization.

The monomers in aqueous solution are polymerized by standard free radical techniques, commonly by using a photoinitiator for activation, such as ultraviolet (UV) light activation. Alternatively, a redox initiator may be used. In this case, however, increased temperatures are desirable.

In one example, the water-absorbent resin is lightly cross-linked to render it water-insoluble. The desired cross-linked structure may be obtained by co-polymerization of the selected water-soluble monomer and a cross-linking agent possessing at least two polymerizable double bonds in the molecular unit. The cross-linking agent is present in an amount effective to cross-link the water-soluble polymer. The amount of cross-linking agent is determined by the desired degree of absorption capacity and the desired strength to retain the absorbed fluid, that is, the desired absorption under load. Typically, the cross-linking agent is used in amounts ranging from about 0.0005 to about 5 parts by weight per 100 parts by weight of monomers (including $\alpha$, $\beta$_unsaturated carboxylic acid monomers and possible co-monomers) used. If an amount over 5 parts by weight of cross-linking agent per 100 parts is used, the resulting polymer has a too high cross-linking density and exhibits reduced absorption capacity and increased strength to retain the absorbed fluid. If the cross-linking agent is used in an amount less than 0.0005 parts by weight per 100 parts, the polymer has a too low cross-linking density and when contacted with the fluid to be absorbed becomes rather sticky, water-soluble and exhibits a low absorption performance, particularly under load. The cross-linking agent will typically be soluble in the aqueous solution.

Alternatively to co-polymerizing the cross-linking agent with the monomers, it is also possible to cross-link the polymer chains in a separate process step after polymerization.

After polymerization, cross-linking and partial neutralization, the viscous SAPs are dehydrated (i.e., dried) to obtain dry SAPs. The dehydration step can be performed by heating the viscous SAPs to a temperature of about 120° C. for about 1 or 2 hours in a forced-air oven or by heating the viscous SAPs overnight at a temperature of about 60° C. The content of residual water in the SAP after drying predominantly depends on drying time and temperature. In one embodiment, "dry SAP" refers to SAP with a residual water content of from about 0.5% by weight of dry SAP up to about 50% by weight of dry SAP, in another embodiment from about 0.5% to about 45% by weight of dry SAP, in another embodiment from about 0.5% to about 30%, in another embodiment from about 0.5% to about 15%, and in yet another embodiment from about 0.5% to about 5%. If not explicitly said to be otherwise, in the following the term "SAP particles" refers to dry SAP particles.

The SAPs can be transferred into particles of numerous shapes. The term "particles" refers to granules, fibers, flakes, spheres, powders, platelets and other shapes and forms known to persons skilled in the art of SAPs. For example, the particles can be in the form of granules or beads, having a particle size of from about 10 μm to about 1000 μm, in another embodiment from about 100 μm to about 1000 μm. In another embodiment, the SAPs can be in the shape of fibers, for example, elongated, acicular SAP particles. In those embodiments, the SAP fibers have a minor dimension (i.e., diameter of the fiber) of less than about 1 mm, in another example less than about 500 μm, and in yet another example less than about 250 μm down to about 50 μm. In one embodiment, the length of the fibers is from about 3 mm to about 100 mm. The fibers can also be in the form of a long filament that can be woven.

However, as the method of one embodiment of the invention is carried out in a drum reactor, the SAP particles should have sufficient free-flowing ability to be able to flow through the drum reactor along the inner surface of the reactor drum. The free-flowing ability must be such that the SAP particles do not form agglomerates with each other, for example, via effects of physical entanglement, which would considerably hinder a uniform UV irradiation of the SAP particles' surface.

The SAP particles of one embodiment have a core and a surface. In one embodiment, the dry SAP particles undergo a surface cross-linking process step, for example, they are cross-linked in their surface while the number of cross-links in the core of the particle is not substantially increased by the method of the invention.

The term "surface" describes the outer-facing boundaries of the particle. For porous SAP particles, exposed internal surfaces may also belong to the surface. As used herein, the term "surface" of the SAP particles refers to the complete and continuous outwardly facing 6% volume of the dry SAP particle, whereas "core" refers to 94% of the volume and comprises the inner regions of the dry SAP particle.

Surface cross-linked SAP particles are well known in the art. In surface cross-linking methods of the prior art, a surface cross-linker is applied to the surface of the SAP particles. In a surface cross-linked SAP particle the level of cross-links in the surface of the SAP particle is considerably higher than the level of cross-links in the core of the SAP particle.

Commonly applied surface cross-linkers are thermally activatable surface cross-linkers. As used herein, the term "thermally activatable surface cross-linkers" refers to surface cross-linkers, which only react upon exposure to increased temperatures, typically around 150° C. Thermally activatable surface cross-linkers known in the prior art are, for example, di- or polyfunctional agents that are capable of building additional cross-links between the polymer chains of the SAPs. Typical thermally activatable surface cross-linkers include, for example, di- or polyhydric alcohols, or derivatives thereof, capable of forming di- or polyhydric alcohols. Examples of such agents are alkylene carbonates, ketales, and di- or polyglycidlyethers. Moreover, (poly)glycidyl ethers, haloepoxy compounds, polyaldehydes, polyoles and polyamines are also well known thermally activatable surface cross-linkers. The cross-link is, for example, formed by an esterification reaction between a carboxyl group (comprised by the polymer) and a hydroxyl group (comprised by the surface cross-linker). Typically, a relatively big part of the carboxyl groups of the polymer chain is neutralized prior to the polymerization step, commonly only few carboxyl groups are available for this surface cross-linking process known in the art. For example, in a 70% percent neutralized polymer only 3 out of 10 carboxylic groups are available for covalent surface cross-linking.

In one embodiment, the method is used for surface cross-linking of SAP particles. Hence, the polymer chains comprised by the SAP particles already have been cross-linked by a cross-linker known in the art, comprising at least two polymerizable double bonds in the molecule unit.

In another embodiment, direct covalent bonds between carbon atoms comprised in the backbone of different polymer chains are formed in the surface of the SAP particles.

As used herein, the term "direct covalent bond" refers to a covalent bond wherein polymer chains are bound to each other only via a covalent bond with no intermediate atoms, such as atoms comprised by a cross-linking molecule. In contrast, known cross-linking reactions between polymer chains always result in covalent bonds between these polymer chains, wherein the reaction product of the cross-linking molecule is built in between the polymer chains. Thus, known surface cross-linking reactions do not result in a direct covalent bond but in an indirect covalent bond comprising the reaction product of the cross-linking molecule. The direct covalent bond is formed between a carbon atom in the backbone of a first polymer chain and a carbon atom in the backbone of a second polymer chain. The bonds are formed intra-particulate within the SAP particle, more specifically they are formed in the surface of the SAP particles, while the core of the SAP particles is substantially free of such direct covalent bonds.

As used herein, the term "backbone" of a polymer chain refers to those carbon atoms which immediately form the polymer chain. Principally, if a reaction resulted in the removal of a carbon atom, which is part of the polymer chain backbone, this reaction would also result in the break of the polymer chain on the position, where this carbon atom had previously been built into the polymer chain.

Optionally, surface cross-linking molecules may also be used. In such embodiments wherein surface cross-linking molecules are added to the SAP particles, additional covalent bonds are formed between the polymer chains comprised in the surface of the SAP particles. These additional covalent bonds comprise the reaction product of said surface cross-linking molecules.

The cross-linking of different polymer chains is not intended to bond different SAP particles to each other. Thus, the method according to one embodiment does not lead to any appreciable inter-particulate bonds between different SAP particles but only results in intra-particulate direct covalent bonds within an SAP particle. If present, such inter-particulate direct covalent bonds would hence require additional inter-particulate cross-linking materials.

In another embodiment, the method which directly bonds polymer chains to each other by a covalent bond between two carbon atoms can be applied for surface cross-linking SAP particles instead of or additional to conventional surface cross-linking.

Radiation Activatable Radical Former Molecules

In one embodiment, the radical former molecules are applied to initiate the surface cross-linking reaction: The radiation activatable radical former molecules are able to form carbon centered radicals located in the polymer backbone of polymer chains comprised in the surface of the SAP particles. This reaction takes place upon UV irradiation. Two of these carbon centered radicals comprised in different polymer chains are able to react with each other and thereby form a direct covalent bond between the polymer chains.

Upon irradiation, some of the radical formers form, in a first step, an intermediate radical, which is typically oxygen-centered, and which may, in a second step, react with a carbon atom comprised in the polymer backbone in the surface of the SAP particle to form a carbon centered radical in the polymer backbone.

In principle, any photo-initiator which is typically used to start the polymerization of vinyl monomers can be applied as a radical former for surface cross-linking according to various embodiments. Such photoinitiators typically serve to trigger radical chain polymerizations of vinyl monomers. It is believed that the reactive intermediate species, which is formed upon irradiation of the photoinitiator with UV radiation, is capable of abstracting hydrogen atoms from C—H bonds of C atoms comprised by the polymer backbone of polymer chains in the surface of the SAP particle (therewith initiating the cross-linking according to one embodiment).

In another embodiment, the radiation activatable radical former molecule comprises a peroxo bridge (O—O), which is homolytically cleaved upon UV irradiation (so-called photo-fragmentation).

However, reactive intermediate species can also be ketones which—upon UV irradiation—have been transferred into short-lived, a so-called excited triplet state. The keton in the triplet-state is also capable of abstracting hydrogen from C—H bonds of C atoms comprised by the polymer backbone whereby the ketone is converted into an alcohol (so-called photo reduction).

In one embodiment, the radical former is water soluble. The water soluble radical former should exhibit a solubility in water of at least about 1 wt %, in another embodiment at least about 5 wt %, in yet another embodiment at least about 10 wt % at 25° C.

Radical formers, which are not initially water soluble, can be rendered water soluble by derivatization, for example, by introducing a charged group into the molecular structure, such as carboxylate or ammonium. As an example, benzophenone can be easily derivatized into benzoyl benzoic acid. However, in one example the radical formers are inherently water soluble, i.e., the introduction of a functional group is not required to render them water-soluble. Typical inherently water soluble radiation activatable radical formers are peroxides like alkali-metal or other inorganic peroxodisulfates or derivatized organic peroxodisulfates. Water-soluble azo-initiators can be used as well (such as the commercially available V-50 or VA-086, Wako Specialty Chemicals). Inorganic peroxides typically fulfill the requirement of water solubility, while organic compounds typically require derivatization. In one example, the water-soluble radical former is sodium peroxodisulfate.

The advantage of providing the radical former in an aqueous solution (and hence, the advantage of using a water-soluble radical former) is two-fold: On the one hand, the aqueous solution facilitates an efficient wetting of the SAP particle surface. Thus, the radical former molecules are actually transported into the particle surface, where they initiate the surface cross-linking reaction.

On the other hand, efficient wetting of the SAP particle surface enhances the chain mobility of the polymer chains comprised in the surface of the SAP particles. This facilitates the bimolecular reaction between the carbon atoms comprised in the polymer backbone and the reactive intermediate species, into which the radical former is transformed upon irradiation. This effect is particularly advantageous for SAP particles comprised of poly(meth)acrylic acid, which are in fact the most widely used SAP particles of today. Polyacrylic acid possesses a glass transition temperature of 106° C. and the sodium salt of polyacrylic acid, at a neutralization degree of 100%, has a glass transition temperature of above 200° C. while in one embodiment the surface cross-linking is typically carried out at temperatures below 100° C. In the presence of water, the glass transition temperature of partly neutralized polyacrylic acid can be significantly decreased. For example, the glass transition temperature of a 65% neutralized sodium polyacrylate can be reduced from ca. 150° C. in the presence of 5 wt % water to below room temperature in the presence of 35 wt % water. However, to make use of this effect, the actual local water concentration directly in the surface of the SAP particle is important.

In one embodiment, to ensure that the cross-linking is actually restricted to the surface of the SAP particles, the water should be prevented from evenly distributing throughout the whole particle volume via diffusion. Therefore, the UV irradiation step should follow not later than one hour after the aqueous solution comprising the radical former has been applied onto the SAP particles, in another embodiment not later than 10 minutes, and in yet another embodiment not later than 1 minute.

In one example, water-soluble radical formers are utilized, as organic solvents are typically more expensive than water and are also more problematic from an environmental standpoint. However, organic radial formers which have not been rendered water-soluble via the above-described derivitization may also be used and can be applied in an organic solvent rather than in water. Examples are benzophenone or any other suitable ketone which is known to undergo photoreduction when irradiated with UV radiation. A further example is dibenzoyl peroxide or any other organic peroxide which is known to undergo photo fragmentation when irradiated with UV radiation.

In one embodiment, the radical former is applied in amounts of less than about 25% by weight of SAP particles, in another embodiment in amounts of less than about 15%, and in yet another embodiment in amounts from about 1% to about 5%. The radical former is typically applied in aqueous solution. In another embodiment, the radical former and the water can be added in two steps, but both ought to be present on the surface during irradiation. In one embodiment, the amount of water is less than about 25% by weight of SAP particles, in another embodiment less than about 15% and in yet another embodiment from about 5% to about 10%. For economic reasons, the amount of water added may be kept as low as possible to shorten or entirely avoid a drying step after the surface cross-linking.

Surface Cross-Linking Molecules

The surface cross-linking molecule is any compound having at least two functional groups which can react with the aforementioned carbon-centered radicals located in the backbone of the polymer chains comprised in the surface of the SAP particles. Upon reaction of the functional group in the surface cross-linking molecule with the carbon-centered radical, a new covalent bond is formed, grafting the cross-linking molecule onto the polymer backbone.

In one embodiment, the functional groups of the surface cross-linking molecules are C=C double bonds. In another embodiment, a cross-linking molecule comprises more than two C=C double bonds. Alternatively, the functional groups can also be CH—X moieties, with X being a hetero atom. An example of a CH—X moiety is an ether, CH—O—R, with R being an alkyl residue.

In one embodiment, cross-linking molecules are polyfunctional allyl and acryl compounds, such as triallyl cyanurate, triallyl isocyanurate, trimethylpropane tricrylate or other triacrylate esters, pentaerythritol triallyl ether, pentaerythritol tetraallyl ether, butanediol diacrylate, pentaerythritol tetraacrylate, tetra allylorthosilicate, di-pentaerythritol pentaacyralate, di-pentaerythritol hexaacyralate, ethyleneglycol diacrylate, ethyleneglycol dimethacrylate, tetra allyloxy ethane, diallyl phthalate, diethyleneglycol diacrylate, allylmethacrylate, triallylamine, 1,1,1-trimethylolpropane triacrylate, triallyl citrate, or triallyl amine.

In another embodiment, the cross-linking molecules are selected from the group consisting of squalene, N,N' methylenebisacrylamide, icosa-pentaenic acid, sorbic acid or vinyl terminated silicones.

In one embodiment, compounds with allylic double bonds are utilized rather than compounds with acrylic double bonds. In another embodiment, the cross-linking molecule is diallyl dimethyl ammonium chloride.

If surface cross-linking molecules are applied, they should be added, for example, by spray application in a solution with an inert solvent (that can be optionally evaporated) before the SAP particles enter the drum reactor described below. The surface cross-linking molecules can be applied in an organic solvent like dichloromethane which is evaporated directly after application. In embodiments, wherein the SAP particles are moisturized, the surface cross-linking molecules can also be applied together with the water as a suspension or, if the surface cross-linking molecules are water soluble, as a solution.

Moreover, if surface cross-linking molecules are applied the molar ratio of surface cross-linking molecules to radical former is in the range of from about 0.2 to about 5, in another embodiment from about 0.33 to about 3, and in yet another embodiment from about 1 to about 3.

In one embodiment, the surface cross-linking compound is water-soluble, so that it can be applied in aqueous solution together with the radical former (if radical formers are used). If a water-insoluble surface cross-linking molecules is applied, it may be emulsified or suspended in the aqueous solution comprising the optional radical former or be applied separately. Water-insoluble surface cross-linking molecules can also be applied in an organic solvent like dichloromethane which is evaporated directly after application.

The surface cross-linking molecules and/or the radical former may be sprayed onto the SAP particles by means of a fluidized-bed spraying chamber. Simultaneously IR-irradiation may be applied to accomplish drying. Instead or in combination with IR-light, any conventional drying equipment can be used for drying. However, in certain embodiments little or no drying is required, for example, in cases, where only small amounts of surface cross-linking molecules and/or the radical former are applied, dissolved in small amounts of solution.

In one embodiment, the surface cross-linking molecules and/or the radical formers are always applied onto the SAP particles outside the drum reactor prior to irradiation inside the drum reactor.

Reaction Mechanism with Radical Formers and with Optional Surface Cross-Linking Molecules:

The radical former molecules undergoing photo-fragmentation comprise a labile bond, and are hereinafter generally depicted as $R_a$—$R_b$. Upon UV irradiation, the labile bond breaks, whereby two radicals ($R_a\cdot$ and $R_b\cdot$) are formed according to Formula 1.

Formula 1:

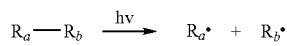

This homolytic cleavage may result in two identical radicals, if the labile bond comprised by the radical former molecule (so-called precursor molecule) divides the molecule into two identical parts. Alternatively, the homolytic cleavage may result in two different radicals.

The radicals, which have been formed, can now react with an aliphatic C—H group comprised in the backbone of the polymer chains in the surface of the SAP particle forming a carbon-centered radical in the polymer backbone according to Formula 2. Two such carbon-centered radicals can react with each other to form a direct covalent bond between the carbon atoms comprised in the polymer backbone.

Formula 2:

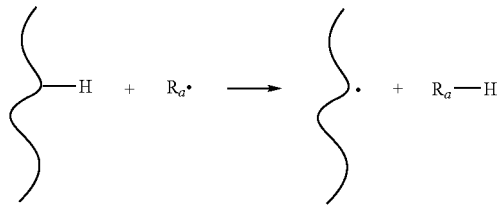

It is also possible that instead of abstracting a hydrogen atom from a carbon-hydrogen bond comprised in the backbone of the polymer chain, a complete carboxyl group is abstracted from the polymer chain (decarboxylation). As a result of this reaction a carbon-centred radical is formed in the backbone of a polymer chain comprised in the surface of the SAP particle.

In one embodiment, surface cross-linking molecules may be additionally used. In such embodiments, the radicals formed from the radical former molecule, can react with one of the C=C double bonds comprised by the cross-linking molecule to form a radical consisting of the reaction product of the cross-linking molecule and the initial radical according to Formula 3.

Formula 3:

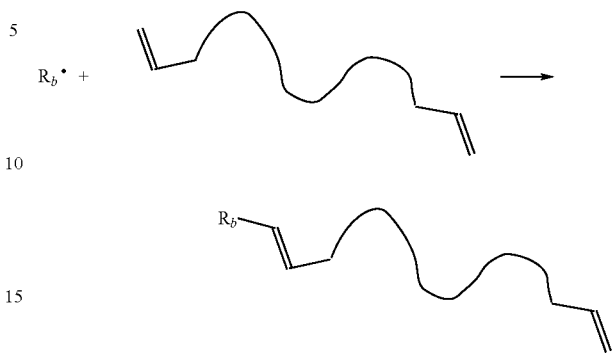

The carbon-centered radical within the polymer chain segment formed in the reaction of Formula 2 can react with the radical formed in Formula 3. The reaction product of this reaction is a polymer chain wherein the reaction products of the radical former molecule and the cross-linking molecule are covalently bound to a carbon atom of the polymer backbone according to Formula 4.

Formula 4:

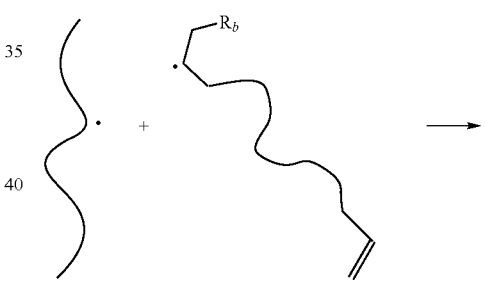

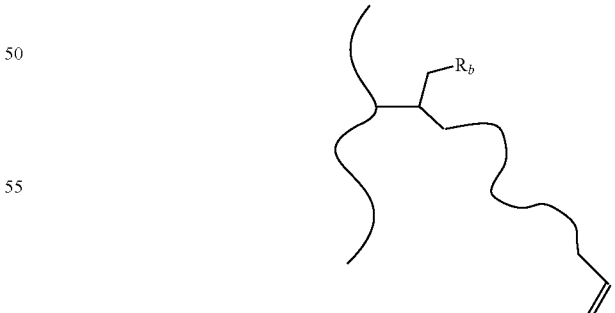

Thereafter, the radicals formed from the radical former molecule in Formula 1, can react with the second of the C=C double bonds of the cross-linking molecule, which is comprised in the reaction product of Formula 4. This reaction is depicted in Formula 5:

Formula 5:

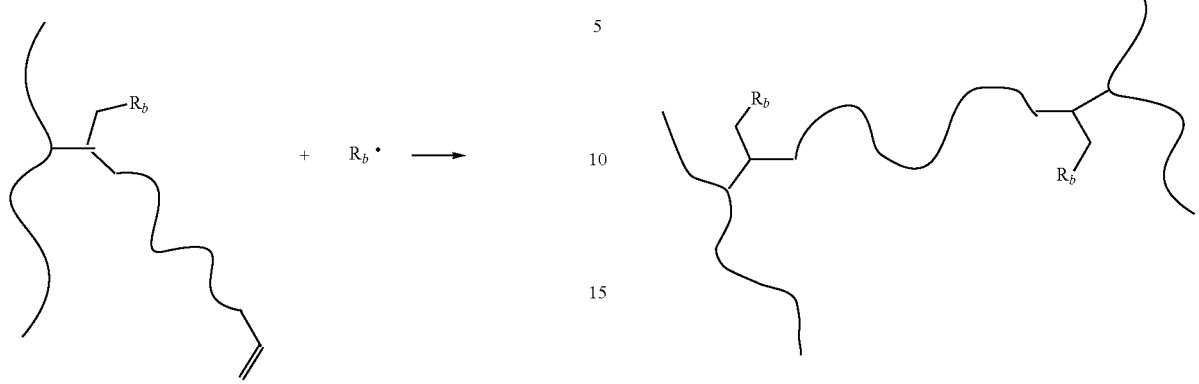

To form the cross-link between two polymer chains, the carbon-centered radical which is comprised in the reaction product of Formula 3 combines with another carbon centered radical comprised in another polymer chain in the surface of the same SAP particle as depicted in Formula 6.

Formula 6:

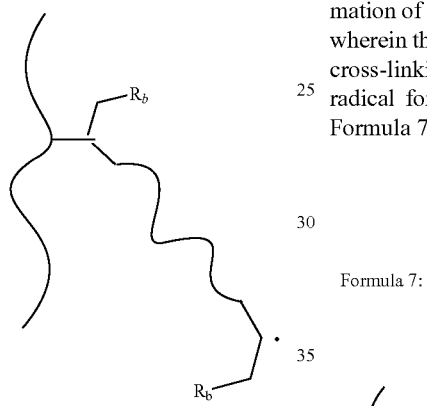

The net reaction when using radical former molecules undergoing photo-fragmentation upon irradiation is the formation of a cross-link between two polymer chain segments, wherein the cross-link comprises the reaction product of one cross-linking molecule with two C=C double bonds and two radical former molecules. The net reaction is depicted in Formula 7:

Formula 7:

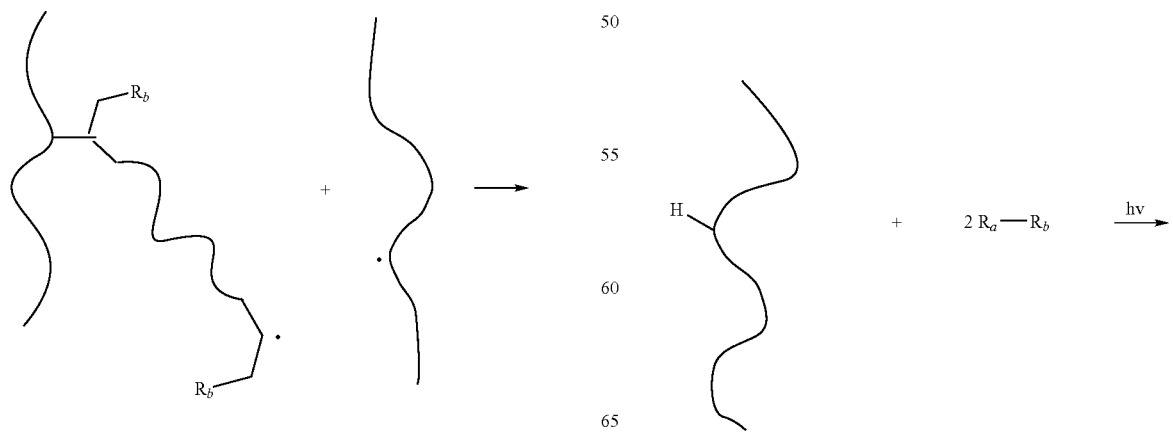

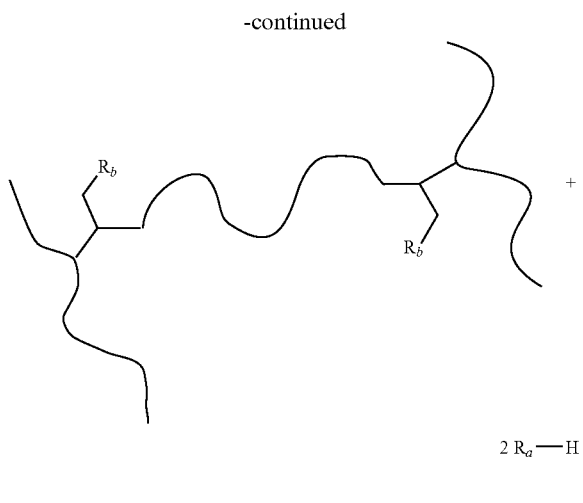

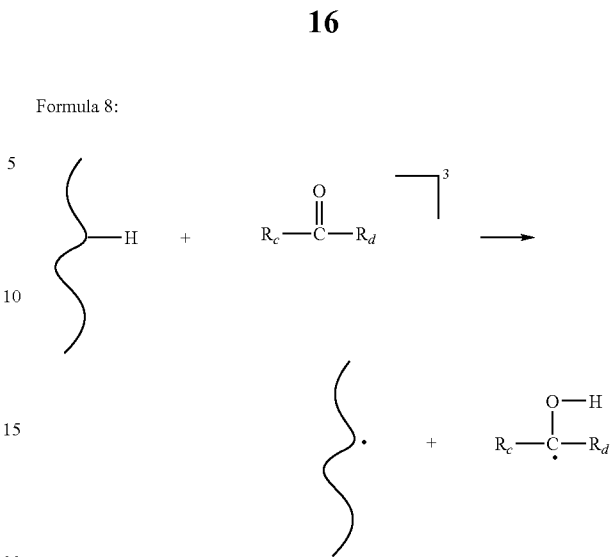

Formula 8:

With the additional use of surface cross-linking molecules the efficiency of the reaction can be further enhanced due to shorter reaction times: Without wanting to be bound by theory, it is believed that the rate determining step of a UV irradiation initiated surface cross-linking reaction in the absence of surface cross-linking molecules is the recombination of two carbon-centered radicals, forming a direct covalent bond between two carbon atoms comprised in two different polymer chains. This recombination follows a kinetic law of a second order, i.e. the reaction rate is proportional to the concentrations of both reactants (i.e. the two combining carbon-centered radicals) multiplied with each other.

If, however, surface cross-linking molecules are added, it is believed, that the reaction between the radical formed from the surface cross-linking molecule and the carbon-centered radical comprised in the polymer chain follows a kinetic law of pseudo-first order, for exanple, the reaction rate is only proportional to the concentration of the carbon-centered radical, since the concentration of the second reaction partner, for example, the radicals formed from the surface cross-linking molecule, is so high that it can be regarded as constant throughout the reaction. Reactions of pseudo-first order kinetics are known to be kinetically favored versus reactions of second order kinetics, for example, they have a higher reaction speed.

Alternatively to radical former molecules undergoing photo-fragmentation it is also possible to use radical former molecules undergoing photo-reduction upon irradiation comprise carbonyl groups. In one embodiment, such radical former molecules are ketones.

Upon UV irradiation, the radical former molecules of this type are transferred in an "excited state" (triplet state). Hence, they are not yet transformed into a radical, but are much more reactive than prior to irradiation.

In the next step, the radical former molecule in its excited state reacts with an aliphatic C—H group comprised in the backbone of a polymer chain in the surface of the SAP particle and abstracts a hydrogen radical, thereby forming a carbon-centered radical at this polymer chain and a ketyl radical according to Formula 8:

The ketyl radical can now react with one of the C=C double bonds of the cross-linking molecule. Principally for the carbon-centered radicals comprised in the backbone of the polymer chains the same reactions take place as shown in FIGS. 3 to 7.

Alternatively (or exclusively in embodiments which do not use surface cross-linking molecules) two ketyl radicals can recombine with one another to form a so-called pinacol, for example, benzpinacol, for benzophenone as initiator.

It should be noted, that in the case of radical former molecules undergoing photo-fragmentation are applied, only a part of the radical former molecule is comprised by the cross-link between the polymer chains, whereas for radical former molecules undergoing photo-reduction, the complete radical former molecule in its reduced form (with a carbonyl group being reduced to a hydroxyl group) is comprised by the cross-link between the polymer chains.

Hence, for radical former molecules undergoing photo-fragmentation, the reaction product comprised by the cross-link between polymer chains is only a part of the initial radical former molecule—typically one half of the initial molecule.

For radical former molecules undergoing photo-reduction, the reaction product comprised by the cross-link between polymer chains is the complete radical former molecule in its reduced form (with a carbonyl group being reduced to a hydroxyl group).

The reaction product of the surface cross-linking molecule—for both types of radical former molecules—is the initial cross-linking molecule, wherein those C=C double bonds, which have reacted with the radicals formed from the radical former molecules (or have reacted directly with the carbon-centered radicals formed in the polymer chain segments) are converted into C—C single bonds.

In embodiments comprising both types of radical former molecules, the surface cross-linking molecules comprise more than two C=C double bonds. In these embodiments, more than two polymer chain segments can be cross-linked to each other, following the reactions described above. In these embodiments, the number of reaction products of radical former molecules comprised by the cross-link equals the number of C=C double bonds comprised by the cross-linking molecule.

Theoretically, the radicals formed from the radiation activatable radical former molecules may also react with carboxyl groups comprised by the polymer chain segments. However, it is much more likely that the radical will react with the aliphatic C—H bond, as it is thermodynamically and kinetically rather unlikely that the radical will be able to abstract a hydrogen radical from a O—H bond comprised by a carboxyl group, as the carboxyl group is strongly polarized.

Principally, it is also possible that instead of abstracting a hydrogen atom from a carbon-hydrogen bond comprised in the backbone of the polymer chain, a complete carboxyl group is abstracted from the polymer chain (decarboxylation). The result of this reaction is the same as if a hydrogen atom is abstracted, for example, a carbon-centred radical is formed in the backbone of a polymer chain comprised in the surface of the SAP particle.

According to one embodiment, only one type of cross-linking molecules may be used or, alternatively, two or more chemically different cross-linking molecules can be applied. Likewise, the only one type of radiation activatable radical former molecule can be used or, alternatively, two or more chemically different radiation activatable radical former molecules can be applied.

In one embodiment, the number of available reaction sites for surface cross-linking the SAP particles is considerably increased compared to surface cross-linking known in the art. Therefore, it is possible to achieve a far more homogenous, uniform surface cross-linking compared to the surface cross-linking known in the art. Due to the homogenous distribution of the surface cross-links in the SAP particle surface, the overall number of surface cross-links does not necessarily have to be increased compared to surface cross-linking know in the art, in order to improve the overall stiffness and gel-strength of the SAP particles.

To ensure that SAP particles with evenly distributed surface cross-linking are obtained, the radical former and the optional surface cross-linking molecules have to be distributed evenly on the SAP particle. Therefore, the surface cross-linker is preferably applied by spraying onto the SAP particles.

Also, compared to the surface cross-linking known from the prior art, the surface cross-linking according to one embodiment is significantly faster. Prior art surface cross-linking reactions carried out under increased temperatures commonly take up to 45 minutes. This time consuming process step renders the manufacturing process of SAP particles less economic than desirable. In contrast, the cross-linking process according to one embodiment can be carried out within a significantly shorter reaction time, typically within minutes, and hence, enables an overall improvement with respect to manufacturing times of the SAP particles. This results in lower energy costs and higher throughput.

Furthermore, as the surface cross-linking reaction proceeds quickly, the radical former molecules and -optionally- surface cross-linking molecules applied on the surface of the SAP particles have less time to penetrate inside the SAP particles. Hence, compared to prior art surface cross-linking, it is easier to actually restrict surface cross-linking to the surface of the SAP particles and to avoid undesired further cross-linking reactions in the core of the SAP particles.

In one embodiment, the $\alpha,\beta$-unsaturated carboxylic acid monomers are often neutralized prior to the polymerization step (pre-neutralization). This step is referred to as the neutralization step. Compounds, which are useful to neutralize the acid groups of the monomers, are typically those, which will sufficiently neutralize the acid groups without having a detrimental effect on the polymerization process. Such compounds include alkali metal hydroxides, alkali metal carbonates and bicarbonates. Preferably, the material used for neutralization of the monomers is sodium- or potassium-hydroxide, or sodium- or potassium-carbonate. As a result, the carboxyl groups comprised by the $\alpha,\beta$-unsaturated carboxylic acid of the polymer are at least partially neutralized. In case sodium hydroxide is used, neutralization results in sodium acrylate, which dissociates in water into negatively charged acrylate monomers and positively charged sodium ions. As the surface cross-linkers known in the art react with the carboxyl groups of the polymer, the degree of neutralization has to be balanced with the need to surface cross-link, because both process steps make use of the carboxyl groups.

If the final SAP particles are in the swollen state, after they absorbed aqueous solution, the sodium ions are freely movable within the SAP particles. In absorbent articles, such as diapers or training pants, the SAP particles typically absorb urine. Compared to distilled water, urine comprises a relatively high amount of salt, which at least partly is present in dissociated form. The dissociated salts comprised by the urine make absorption of liquid into the SAP particles more difficult, as the liquid has to be absorbed against an osmotic pressure caused by the ions of the dissociated salts. The freely movable sodium ions within the SAP particles strongly facilitate the absorption of liquid into the particles, because they reduce the osmotic pressure. Therefore, a high degree of neutralization can largely increase the capacity of the SAP particles and the speed of liquid absorption.

Furthermore, a higher degree of neutralization typically reduces the materials expenses and, consequently, also reduces the overall manufacturing costs for SAP particles: Sodium hydroxide, which is commonly used to neutralize the polymer, is typically less expansive compared to acrylic acid. Hence, increasing the neutralization degree increases the amount of sodium hydroxide comprised by a given amount of SAP. Consequently, less acrylic acid is required for making SAPs.

In one embodiment, the reduction of undesired side-reactions during the surface cross-linking process is advantageous. Surface cross-linking known in the prior art requires increased temperatures, commonly around or above 150° C. At these temperatures, not only surface cross-linking is achieved, but also a number of other reactions take place, for example, anhydride-formation within the polymer or dimer cleavage of dimers previously formed by the acrylic acid monomers. These side-reactions are highly undesired, because they result in SAP particles with decreases capacity.

As the surface cross-linking process according to one embodiment does not necessarily need increased temperatures but can also be carried out at moderate temperatures, those side-reactions are considerably reduced. According to one embodiment, the surface cross-linking reaction can be accomplished at temperatures of less than about 100° C. to avoid the undesired side reactions.

Also, at elevated temperatures around or above 150° C. commonly applied in the surface cross-linking process known in the prior art, the SAP particles sometimes change their color from white to yellowish. Due to the reduced temperatures required for surface cross-linking in the method of one embodiment, the problem of color degradation of the SAP particles can be considerably reduced.

The surface cross-linking according to one embodiment can be carried out together with one or more thermally activatable surface cross-linkers known in the art, for example, 1,4-butandiol. In this embodiment, however, both, UV radiation and increased temperatures (typically above 140° C.), are required. In these embodiments, the surface of the resulting SAP particles will further comprise the reaction product of the thermally activatable surface cross-linker.

The method of one embodiment may further comprise an optional washing step to wash off un-reacted surface cross-linking molecules and/or radical former molecules or to wash off molecules formed by side reactions.

UV Irradiation

In one embodiment, the SAP particles are exposed to ultra-violet-(UV-) radiation. The UV-domain of the electromagnetic spectrum is defined between wavelengths of 100 and 380 nm and is divided into the following ranges: UV-A (315 nm-400 nm), UV-B (280 nm-315 nm), UV-C (200 nm-280 nm) and Vacuum UV (VUV) (100 nm-200 nm).

UV radiation within the UV-A, UV-B or UV-C range depending on the presence, concentration and nature of a photo-initiator, commercially available mercury arcs or metal halide radiation sources can be used. The choice of the radiation source depends on the absorption spectrum of the radical initiator and on the reactor geometry to be used. In one embodiment, the UV-B range proved to be effective in combination with the above described initiators.

The radiation sources can be optionally cooled with gas, and, to this end, may be embedded in or may contain a cooling sleeve.

Drum Reactor and Method

In one embodiment, the photochemical reactor, in which the surface cross-linking method of one embodiment is carried out, is a drum reactor as schematically depicted in FIG. 1.

The drum reactor 10 comprises a hollow drum 20 having a cross-section which in one embodiment is round (for example, circular) or ellipsoid shaped. The cross-section of the drum 20 can also be polygonal, for example, triangular; quadrangular or higher numbers of angles. However, in polygonal embodiments the number of angles is rather high, in one embodiment the number of angles n is >4, in another embodiment n is >6, and in yet another embodiment n is >8. The drum may be made of all sorts of material, for example, of glass, synthetic materials like Plexiglas™ or metal. In one embodiment, the material is opaque or transparent. The drum 20 has a longitudinal axis 30. The longitudinal extension of the drum is generally larger than the cross-section. In drums having an ellipsoid-shaped diameter, the longitudinal extension is generally larger than the largest diameter. The drum further comprises a lower longitudinal part 120 and an upper longitudinal part 130 (however, as the drum is rotated in use, the lower and upper longitudinal parts constantly refer to different physical parts of the drum).

In one embodiment, the UV irradiation source 40 is mounted within the drum 20, in another embodiment either along the longitudinal axis 30, parallel to the longitudinal axis 30 or slightly tilted to the longitudinal axis 30. In yet another embodiment, the irradiation source 40 can also be installed outside the drum, but has to be installed such that irradiation is able to reach the SAP particles within the drum. In embodiments, wherein the irradiation source is installed within the drum, the dimensions of the irradiation source 40 have to be chosen accordingly in order to facilitate the assembly within the drum 20. Depending on the dimensions of the drum 20 and the intended flow rate of SAP particles through the drum, either one irradiation source or two or more irradiation sources may be required. In one embodiment, rod-shaped irradiation sources 40 are used in the drum 20. In another embodiment, a non rod-shaped irradiation source 40 is used in the drum 20.

Though the drum 20 can also be positioned horizontally, in another embodiment the drum 20 is installed in a tilted manner, i.e. the longitudinally axis 30 is not horizontally but tilted at an angle α (in a horizontal embodiment, the angle α is zero). In a tilted embodiment, one end of the drum 20 is the upper end 50 while the opposite end is the lower end 60.

The reactor further comprises a means for feeding the SAP particles into the drum 20. The feeding means 70 is provided on one end of the drum. In tilted embodiments, the end provided with the feeding means 70 is the upper end 50. The feeding means 70 can, for example, be a conveying screw or any other suitable means.

In one embodiment, drying of the SAP particles is carried out before the SAP particles are fed into the drum reactor. Conversion of dry SAP particles through the drum reactor is easier than for swollen SAP particles as the tendency of the SAP particles to agglomerate is considerably reduced.

In case drying is nevertheless carried out after the SAP particles have undergone surface cross-linking according to one embodiment, the probability of agglomeration can be reduced by using fluidity enhancers.

The reactor further comprises a collection means 80. In one embodiment, the collection means 80 is provided on the end of the drum 20 opposite to the SAP particle feeding means 70 and collects the SAP particles leaving the drum 20 after they have undergone surface cross-linking. In tilted embodiments, the end provided with the collecting means 80 is preferably the lower end 60. The collecting means 80 can, for example, be a funnel or any other suitable means.

Alternatively, in embodiments wherein the irradiation source 40 is not provided along the complete longitudinal extension of the drum 20, the collecting means may also be provided within the drum towards the lower end 60, which in this case would not be open to allow the particles to leave the drum but would be closed. In such embodiments, the SAP particles are fed into the drum 20 continuously or discontinuously, are irradiated while they move through the drum and accumulate in the drum part towards the lower end 60, where no irradiation source is installed or where the irradiation source is concealed such, that the SAP particles in this drum part are not subjected to irradiation. If a certain amount of SAP particles has accumulated, the lower end of the drum is opened and the SAP particles are able to leave the drum.

According to one embodiment, the drum 20 is rotated around its longitudinal axis 20. Therefore, the drum reactor 10 is provided with a driving means (not shown in FIG. 1) which drives the rotation of the drum 20. The driving means can be any suitable means known in the art, for example, a motor. Moreover, to stabilize the drum 20, supporting means may optionally be provided, for example, supporting rolls 90. Typically, the drum will be mounted within a frame (not shown in FIG. 1). While the drum is rotated, the UV irradiation source within the drum does not need to rotate while the method is carried out.

In embodiments, wherein the irradiation source 40 is provided within the drum 20, the drum reactor 10 is also equipped with a screen 100, which in one example is a parabolic mirror. The screen 100 is mounted above the UV irradiation source within the drum 20. Like the UV irradiation source, also the screen is not rotated around the UV irradiation source as the drum is rotated.

In one embodiment, the method is carried out in a continuous process, i.e., the SAP particles are continuously fed into the drum reactor and are also leaving the drum continuously, the method can also be carried out discontinuously in a batch process. In this case, a certain amount of SAP particles is fed into the drum 20, is irradiated within the rotating drum 20 and is taken out of the drum 20 prior to the next batch of SAP particles enter the drum 20.

According to one embodiment, SAP particles are supplied to the drum via the feeding means 70. As the SAP particles move through the drum 20, the drum rotates around its axis, thereby gently agitating the SAP particles. On their way through the drum, the SAP particles are irradiated with UV by the irradiation source 40, whereby the surface cross-linking reaction is initiated and takes place. At the end of the drum 20, the SAP particles leave the drum and are collected by the collecting means 80.

The SAP particles normally possess a particle size distribution, typically ranging from about 10 to about 1000 µm. To increase the reproducibility of the method, effects of particle size discrimination that may occur during irradiation are to be avoided. Specifically, it should be avoided that larger particles pass the reactor faster and, hence, receive a smaller dose of radiation than smaller particles.

Without wishing to be bound by theory, it is believed that contrary to polymerization reactions, wherein thousands of covalent bonds are created per absorbed photon via chain reaction mechanisms, the reaction in accordance with one embodiment generally requires stoichiometric amounts of photons of UV radiation. Albeit, exposure of the complete surface area of all particles needs to be achieved in order to obtain a uniform cross-linked structure on the surface.

Operational parameters of the drum 20 reactor include the tilt angle α, the position of the irradiation source 40 within the drum 20, the position of the optional screen relative to the lamp, the composition of the gas atmosphere in the drum 20, the rotating speed of the drum 20 and the emittance of the radiation source (corresponding to the power of the lamps). A further parameter is the characteristic of the inner surface of the drum wall. If a screen 100 is used, the position of the screen 100 relative to the irradiation source 40 is a further variable. Additional heating is typically not required.

The tilt angle α is the angle between a horizontal line and the longitudinal axis 30 of the drum. The tilt angle α of the drum 20 decides on the impact of gravity on the SAP particle movement. The tilt angle can be from about 0° to about 80°. In one embodiment, the tilt angle α is more than about 0°, in another embodiment the tilt angle is from about 0.5° to about 45°, and in yet another embodiment from about 1° to about 30°.

In one embodiment, the primary driving force for the SAP particle movement is gravity. The tilt angle can, however, also be as low as 0. In these embodiments, the SAP particles are fed into the drum reactor and a "wall" is mounted at the feeding side of the drum reactor to initially force the SAP particles into the right direction. Once the particles are inside the drum, the rotation of the drum together with the defined direction of movement, with which the SAP particles are fed into the drum, forces the SAP particles into a helical path which results in the SAP particles being carried through the drum.

If a drum with a tilt angle of 0° is used in a batch process, the SAP particles can also be spread out uniformly along the length of the drum prior to starting the rotation (no initially defined direction of movement). As the SAP particles in these embodiments are not fed into the drum while it is rotating, the SAP particles are not forced into a helical path. After the SAP particles have undergone UV irradiation, the SAP particles are taken out of the drum.

The position of the radiation source 40 within the drum 20 decides on the distance between the SAP particles and the irradiation source 40. The SAP particles moving through the drum are not distributed evenly over the inner complete surface of the drum but, due to gravity, are mainly moving along the lower parts of the drum. Hence, most of the SAP particles will not follow a complete helical path within the drum but will only partly follow a helical path, as once they have reached a certain "height" while climbing up the "wall" of the drum, the SAP particles will fall back down due to gravity.

Hence, if the irradiation source 40 is positioned towards the lower part 120 of the drum (referring to the drum in a non-rotating state), the distance between the irradiation source and the SAP particles is relatively small. If the irradiation source is positioned towards the upper part 130 of the drum (referring to the drum in a non-rotating state), the distance between the irradiation source and the SAP particles is increased.

In one embodiment, the power of the UV lamps depends on the dimensions of the drum reactor and the intended amount of SAP particles moving through the drum at a given time interval. For smaller drum reactors with small flow through, UV lamps having a power from 1 kW to 2 kW may be used, however, for relatively large drum reactors, UV lamps with a power of up to 24 kW or even higher may be used. In one embodiment, irradiation time within the drum reactor is from about 1 min. to about 30 min., in another embodiment from about 2 min. to about 15 min., in yet another embodiment from about 2 min. to about 5 min. In one embodiment, the distance between the UV-lamp(s) and the SAP particles which are to be cross-linked varies from about 1 cm to about 15 cm.

Generally, a rotation of the drum forces the individual SAP particle to follow a quasi helical path rather than rolling straight through the drum. Hence, the residence time of the SAP particles in the drum can be increased by increasing the rotation speed. However, the rotating speed of the drum is not intended to be increased to a degree where the centrifugal force is such that the SAP particles are evenly distributed along the inner surface of the drum. Though the rotation principally favors a helical movement of the SAP particles, the rotation speed should be adjusted to keep the majority of the SAP particles within the lower part of the drum and "climbing up" at the inner surface is limited.

The rotation of the drum facilitates gentle shear movement of the SAP particles and hence, ensures that the SAP particles are tuned over to achieve homogeneous exposure to UV radiation of the complete SAP particle surface. At the same time the SAP particles suffer minimum of abrasion that might otherwise destroy the newly created cross-links in the surface of the SAP particles.

In one embodiment, the rotation speed of the drum is from about 1 rpm to about 180 rpm, in another embodiment from about 5 rpm to about 100 rpm, and in yet another embodiment from about 10 rpm to about 60 rpm. However, the appropriate rotation speed is strongly depending on the cross section of the drum.

The residence time of the SAP particles in the drum is further controlled by the roughness of the inner surface of the drum. If the inner surface of the drum is relatively rough, the SAP particles will move slower (at a given rotation speed) compared to an inner surface which is relatively even. The rougher the surface, the steeper is the helical side movement of the SAP particles at a given rotation speed. Moreover, the residence time of the SAP particles in the drum can be further increased by introducing raised or lowered obstacles in certain parts of the drum's inner surface. This may be done especially if the tilt angle α of the drum is relatively large in order to slow down the SAP particle movement through the drum.

One embodiment of an obstacle is a helically shaped obstacle (not shown in FIG. 1) within the drum. The helically shaped obstacle is positioned in close contact with the inner surface of the drum. It can be engraved within the inner surface of the drum or may, alternatively, be raised above the surface of the drum. The helically shaped obstacle can be rotated together with the rotation of the drum (for example, in embodiments, wherein it is fixed onto the inner surface of the drum or wherein in is engraved into the inner surface of the drum), or, in another embodiment the helically shaped obstacle can be rotated with a direction of rotation opposite to the direction of rotation of the drum (which obviously does not work for embodiments, wherein the helically shaped obstacle is engraved into the inner surface of the drum). Also, the helically shaped obstacle can be configured such that it does not rotate at all while the drum is rotating (again, this is not possible for embodiments, wherein the helically shaped obstacle is engraved into the inner surface of the drum). The helically shaped obstacle can be configured such that the residence time of the SAP particles within the drum is prolonged compared to the same drum without a helically shaped obstacle.

In embodiments comprising a helically shaped obstacle and wherein the drum is arranged in a tilted manner ($\alpha > 0°$), it is possible to feed the SAP particles into the lower end 60 of the drum and move the SAP particles upwards through the drum along the inner surface. In such an embodiment, the helically shaped obstacle has to rotate in the same direction as the drum. The helically shaped obstacle ensures that the SAP particles move through the drum along a helical path. After UV irradiation, the SAP particles leave the drum on its upper end 50, where the collecting means 80 is provided. In these embodiments, the transport of the SAP particles is facilitated via the helically shaped obstacle against gravity. The described helix within the drum can of course also be used for reactor embodiments with a tilt angle $\alpha$ of 0°.

Also, if a discontinuous process is used and the drum is mounted in a tilted manner ($\alpha > 0°$), the SAP particles can be fed into the drum at the lower end 60, move upwards while they are irradiated due to the helically shaped obstacle installed within the drum, and are allowed to leave the drum also through the lower end (e.g., by stopping the rotation the SAP particles will flow back downwards). Then the next batch of SAP particles can be fed into the drum at the lower end 60. In such embodiments, both, the feeding means 70 and the collecting means 80 are provided at the same (lower) end of the drum.

However, the number of SAP particle layers in the drum should be kept rather low to minimize shadowing effects as SAP particles overlaying each other result in the subjacent particle getting less UV irradiation. On the other hand, high throughputs are desired for economic reasons. For a given reactor geometry, the technical/commercial efficiency can be improved by ensuring that the SAP particles are sufficiently mixed in the drum so that each particle receives substantially the same UV dose. To this end, it may be advisable to extend the length of the drum in order to ensure that the all SAP particles are efficiently irradiated to obtain the desired surface cross-linking.

Fluidity enhancers, as they are widely known in the art, such as hydrophilic amorphous silicas, as they are commercially available, for example, from Degussa Corp., can optionally be added to the SAP particles in the drum to assist in avoiding agglomerates, for example, if the water content of the SAP particles is relatively high. The fluidity enhancers are typically applied in a range of from about 0.1 weight-% by weight of SAP particles to about 10 weight-% by weight of SAP particles.

If SAP particle throughput increases, the power of the lamps and/or number of lamps should be adjusted accordingly to ensure that all SAP particles are still subjected to an UV dose efficient to achieve the desired surface cross-linking.

In one embodiment, the drum is provided with a screen 100 mounted above the irradiation source 40, if the irradiation source is provided within the drum 20.

The screen conceals the irradiation source 40 in the areas above the screen. Hence, the upper part of the drum 130—and consequently also the SAP particles moving along the surface of the upper part of the drum 130—is not irradiated. The degree of preventing SAP particles from being irradiated can be adjusted by choosing the size of the screen accordingly. In case the SAP particles fed into the drum possess a larger particle size distribution, smaller particles generally have a greater tendency than larger particles to adhere to the inner surface of the drum and following a more helical path through the drum. Consequently, smaller SAP particles have a longer residence time within the drum compared to larger SAP particles. The screen prevents smaller SAP particles that adhere to the wall from receiving an over-proportionally high UV dose, since they are shadowed as they "climb the wall".

In one embodiment, the screen consists of a parabolic mirror. In the absence of radiation absorbing gases, the mirror may reflect the radiation onto the SAP particle stream moving on the lower part of the drum 120, thereby increasing the radiation efficiency.

Also, the screen 100 protects the radiation source from particles falling down from the upper part 130 of the inner surface.

In one embodiment, the method is carried out under normal atmosphere to reduce costs. Also, without wishing to be bound by theory, it is believed that normal atmosphere enables improved surface cross-linking results as oxygen, which is a bi-radical, may participate in the reaction mechanism by formation of intermediate peroxile radicals upon irradiation. Hence, the number of available radicals is proliferated, which in turn enable the formation of carbon-centered radicals in the polymer backbone of the polymer chains in the surface of the SAP particles. In one embodiment, the degree of humidity is not crucial for UV irradiation, as water molecules do not absorb UV-A, -B or -C radiation.

In one embodiment, if the method is not carried out under normal atmosphere, a means 110 for providing and maintaining the desired gaseous environment (e.g., nitrogen or an enhanced water vapour pressure) is provided. It is possible to keep only the drum under the desired atmosphere or, alternatively and as shown in FIG. 1, to keep the complete reactor 10 or at least the drum 20 and its immediate surrounding under inert atmosphere by placing the reactor 10 or parts of the reactor 10 including the drum 20 into a container, which permits to control the gas phase by means 110.

In one embodiment, the temperature in the drum 20 is from about 20° C. to about 99° C., in another embodiment from about 20° C. to about 75° C., and in yet another embodiment from about 20° C. to about 50° C.

Compared to the equipment required for state of the art surface cross-linking methods, the drum reactor used and described herein weighs less and requires less space. Also, the equipment is less expensive.

Alternatively to the drum reactor 10, a fluidized bed reactor having a radial symmetric geometry with a rod-shaped radiation source in the centre may be considered.

In contrast to the drum reactor 10, a fluidized bed reactor requires the generation of a gas.

A disadvantage of fluidized bed reactors is that SAP particles with larger diameters (i.e., larger weight) precipitate faster and are therefore exposed to a smaller dose of radiation compared to smaller SAP particles. Such inhomogeneous UV exposure for SAP particles of different size might result in a relatively high variability with respect to surface cross-linking for SAP particles of different size. The same arguments apply for the use of vibrating plates to facilitate UV exposure.

In contrast, the drum reactor 10 enables highly reproducible residence times of the SAP particles in the drum. There is only little back-mixing of the SAP particles inside the drum and SAP particles having similar size have very similar residence times in the drum. Moreover, if SAP particles of highly varying size are use, all SAP particles—independent of their size—can be exposed to similar UV doses if the shadowing effect of a screen is exploited.

A further disadvantage of fluidized bed reactors compared to the drum reactor 10 is that fluidized bed reactors require expensive investment for gas flow control.

Also, use of a drum reactor facilitates less abrasion compared to fluidized bed reactors due to gentle shear movement compared to rather vigorous agitation.

The different relevant parameters described above are often connected to each other such that varying one parameter may require that at least one other parameter also has to be changed and adjusted. For example, the power of the UV lamps will have an influence on the overall number of UV lamps required for the method. Further, the dimension and overall number of the UV lamps may have an influence on the diameter and length of the drum. The length of the drum, in turn, may influence the required tilt angle of the drum and the rotation speed, as length of drum, tilt angle and rotation speed all influence the residence time of the SAP particles in the drum. Hence, to achieve a desired change in the method, it may be possible to alternatively change one parameter or the other, or to change more than one parameter.

However, by routinely adjusting the different parameters, the method of one embodiment can be readily and relatively quickly optimized until the SAP particles have the desired degree of surface cross-linking.

Absorbent Articles

In one embodiment, the SAP particles made by the method are applied in absorbent cores of absorbent articles. As used herein, absorbent article refers to devices that absorb and contain liquid, and more specifically, refers to devices that are placed against or in proximity to the body of the wearer to absorb and contain the various exudates discharged from the body. Absorbent articles include but are not limited to diapers, adult incontinent briefs, diaper holders and liners, sanitary napkins and the like.

In one embodiment, absorbent articles are diapers. As used herein, "diaper" refers to an absorbent article generally worn by infants and incontinent persons about the lower torso.

In one embodiment, absorbent articles typically comprise an outer covering including a liquid pervious topsheet, a liquid impervious backsheet and an absorbent core generally disposed between the topsheet and the backsheet. The absorbent core may comprise any absorbent material that is generally compressible, conformable, non-irritating to the wearer's skin, and capable of absorbing and retaining liquids such as urine and other certain body exudates. In addition to the SAP particles, the absorbent core may comprise a wide variety of liquid-absorbent materials commonly used in disposable diapers and other absorbent articles such as comminuted wood pulp, which is generally referred to as air felt.

Exemplary absorbent structures for use as the absorbent assemblies are described in U.S. Pat. No. 5,137,537 entitled "Absorbent Structure Containing Individualized, Polycarboxylic Acid Crosslinked Wood Pulp Cellulose Fibers" which issued to Herron et al. on Aug. 11, 1992; U.S. Pat. 5,147,345 entitled "High Efficiency Absorbent Articles For Incontinence Management" issued to Young et al. on Sep. 15, 1992; U.S. Pat. No. 5,342,338 entitled "Disposable Absorbent Article For Low-Viscosity Fecal Material" issued to Roe on Aug. 30, 1994; U.S. Pat. No. 5,260,345 entitled "Absorbent Foam Materials For Aqueous Body Fluids and Absorbent Articles Containing Such Materials" issued to DesMarais et al. on Nov. 9, 1993; U.S. Pat. No. 5,387,207 entitled "Thin-Until-Wet Absorbent Foam Materials For Aqueous Body Fluids And Process For Making Same" issued to Dyer et al. on Feb. 7, 1995; U.S. Pat. No. 5,397,316 entitled "Slitted Absorbent Members For Aqueous Body Fluids Formed Of Expandable Absorbent Materials" issued to LaVon et al. on Mar. 14, 1995; and U.S. Pat. No. 5,650,222 entitled "Absorbent Foam Materials For Aqueous Fluids Made From High Internal Phase Emulsions Having Very High Water-To-Oil Ratios" issued to DesMarais et al. on Jul. 22, 1997.

Test Methods

The capacity of the SAP particles is often described in terms of the centrifuge retention capacity value (CRC). A test method for CRC is described in EDANA method 441.2-02.

The parameter commonly used to describe the behavior of SAP particles under a certain pressure is AAP (absorbency against pressure). AAP is measured according to EDANA method 442.2-02.

Permeability of the gel bed comprised of SAP particles is generally measured as saline flow conductivity (SFC). A test method to determine SFC is described in U.S. Pat. No. 5,562,646, issued to Goldman et al. on Oct. 8, 1996. In one embodiment, the test method in U.S. Pat. No. 5,562,646 is modified in that a 0.9% NaCl solution is used instead of Jayco solution).

EXAMPLE

Base Polymer:

As base polymer, the water-swellable polymer as described in Example 1.2 of WO 2005/014066 A1, titled "Absorbent articles comprising coated water-swellable material" and filed on 17 Feb. 2005 is used. However, the amount of MBAA has to be routinely adjusted accordingly to obtain SAP particles with a CRC value of 37.5 g/g as in the Example. It should be noted, that the CRC value can principally be adjusted in the same way as the CCRC way, which is described in Example 1.2 of WO 2005/014066 A1.

The drum reactor for use in the Example has a length of 40 cm and a diameter of 11 cm. The drum is made of glass, with the inner surface of the drum rendered slightly rough. The degree of roughness is adjusted to provide a residence time of the SAP particles within the drum of one minute. The inner surface of the drum is provided with equally distributed roughness, i.e., there are no different regions within the drum having a different degree of roughness.

Within the drum, a rod-type 2 kW Medium Pressure Mercury UV Lamp (TQ2024.100, Heraeus Noblelight) of 40 cm length (i.e., as long as the drum) is mounted. The radiation source is installed at the longitudinal axis of the drum. The drum is mounted in a frame with a tilt angle $\alpha$ of 1°.

A mixture of 5 parts of the radical former sodium peroxodisulfate, 8 parts of water and 5 parts of hydrophilic amorphous silica is prepared which is then added under vigorous stirring to 100 parts of SAP particles (=10 g) consisting of base polymer. The sample is then left standing for 10 minutes. The preparation is carried out under normal (ambient) atmosphere and at 20° C. Thereafter, the complete mixture is fed into upper end of the drum via an Archimedes screw at a rate of 20.2 g/min while drum is rotated at a rotating speed of 11 rpm. This rotating speed is kept constant during UV irradiation of the SAP particles. No surface cross-linking molecules are used.

The SAP particles are irradiated within the drum under ambient atmosphere. The mean residence time of the SAP particles within the drum has been determined to be 1 minute.

The mean residence time of the SAP particles within the drum is determined by adding a colored SAP particle to the SAP particles fed into the reactor and measuring, how long it takes until the colored particle leaves the drum. This test is done 5 times and the average time is calculated. As the length of the drum is equal to the length of the radiation source, the mean residence time is equal to mean irradiation time.

The temperature within the drum is kept constant at 20° C. The SAP particles are collected as they leave the drum at the lower end.

The SAP particles are fed through the drum 5 times in sequence, whereby the SAP particles are fed again in the drum immediately after all SAP particles of the sample have left the drum. Hence, the SAP particles are irradiated for fife minutes in total.

The CRC, AAP and SFC values of the initial SAP particles (i.e., the SAP particles prior to mixing with sodium peroxodisulfate, water and hydrophilic amorphous silica and prior to UV irradiation) and the SAP particles after UV irradiation have been determined according to the test methods set out above. The results are summarized in Table 1.

TABLE 1

| Material | CRC (g/g) | AAP at 4.83 kPa (g/g) | SFC ($10^{-7}$ cm$^3$ s g$^{-1}$) |
| --- | --- | --- | --- |
| SAP particles prior to irradiation | 37.5 | 7.6 | 0 |
| SAP particles after 5 minutes irradiation | 28.0 | 18.9 | 19 |

For SAP particles without surface cross-linking (hence, only consisting of the base polymer), the CRC value is typically rather high as the SAP particles are not restricted in swelling due to the cross-links introduced on the surface of the SAP particles. After surface cross-linking, the CRC value of the SAP particles decreases.

In contrast, the SFC and AAP values for non surface cross-linked SAP particles is very low (the value can be as low as zero): As the SAP particles are extremely soft, the they do not absorb well against an applied pressure (low AAP) and gel blocking occurs, which results in a very low SFC value.

Generally, an increase in SFC and AAP value together with a decrease in CRC value compared to non surface cross-linked SAP particles consisting only of the base polymer is an indirect proof that surface cross-linking has actually taken place.

As a result, the Examples show that the base polymer has indeed been surface cross-linked by the method described herein.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm".

All documents cited in the Detailed Description of the Invention, are, in relevant part, incorporated herein by reference; the citation of any document is not to be construed as an admission that it is prior art with respect to the present invention.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. An absorbent article comprising surface cross-linked superabsorbent polymer particles, said superabsorbent polymer particles being made by a method comprising the steps of:
   a) providing superabsorbent polymer particles and providing radical former molecules applied onto said superabsorbent polymer particles;
   b) providing a reactor comprising a drum, said drum having a longitudinal axis and further having a cross-section, wherein an irradiation source is provided such that the radiation emitted by the irradiation source is able to reach superabsorbent polymer particles within said drum, said irradiation source being able to emit UV radiation of a wavelength between about 201 nm and about 400 nm;
   c) feeding said superabsorbent polymer particles with said radical former molecules added thereon into said drum;
   d) moving said superabsorbent polymer particles with said radical former molecules added thereon in said drum by rotating said drum around its longitudinal axis;
   e) said superabsorbent polymer particles with said radical former molecules added thereon being irradiated by said irradiation source as said superabsorbent polymer particles are moved within said drum; and
   f) collecting said superabsorbent polymer particles leaving said drum.

2. The absorbent article of claim 1, wherein in said method said irradiation source is arranged within said drum.

3. The absorbent article of claim 2, wherein in said method said irradiation source is arranged along said longitudinal axis, parallel to said longitudinal axis or at an angle or arc relative to said longitudinal axis.

4. The absorbent article according to claim 1, wherein in said method the distance between said irradiation source and the superabsorbent polymer particles being within the drum is from about 1 cm to about 15 cm.

5. The absorbent article according to claim 1, wherein in said method said drum is round or ellipsoid shaped or is polygonal shaped with the number of angles being more than 6.

6. The absorbent article according to claim 2, wherein in said method a screen is mounted above said irradiation source.

7. The absorbent article according to claim 1, wherein in said method said drum rotates at a speed of from about 1 rpm to about 180 rpm.

8. The absorbent article according to claim 1, wherein in said method the UV irradiation is carried out at a temperature of from about 20° C. to about 99° C.

9. The absorbent article according to claim 1, wherein in said method UV irradiation is carried out under normal atmosphere.

10. The absorbent article according to claim 1, wherein in said method said radical formers are water-soluble and are applied in an aqueous solution.

11. The absorbent article according to claim 10, wherein in said method said radical former is sodium peroxodisulfate.

12. The absorbent article according to claim 1, wherein in said method additional surface cross-linking molecules are applied onto said superabsorbent polymer particles prior to UV irradiation, said surface cross-linking molecules having at least two functional groups, wherein said functional groups are C=C double bonds or are CH—X moieties, with X being a hetero atom.

13. The absorbent article according to claim 1, wherein in said method said superabsorbent polymer particles are fed into said drum continuously and wherein said superabsorbent polymer particles leave said drum continuously.

* * * * *